(12) United States Patent
Radwanski et al.

(10) Patent No.: US 11,679,193 B2
(45) Date of Patent: Jun. 20, 2023

(54) SYSTEM AND METHOD OF COLLECTING AND INFUSING AN APOPTOTIC WHITE BLOOD CELL COMPONENT AND A TRANSPLANT COMPONENT

(71) Applicant: Fenwal, Inc., Lake Zurich, IL (US)

(72) Inventors: Katherine N. Radwanski, Highland Park, IL (US); Tanima Jahan Abedin, Chicago, IL (US); Christopher J. Wegener, Libertyville, IL (US)

(73) Assignee: Fenwal, Inc., Lake Zurich, IL (US)

( * ) Notice: Subject to any disclaimer, the term of this patent is extended or adjusted under 35 U.S.C. 154(b) by 1009 days.

(21) Appl. No.: 16/226,452

(22) Filed: Dec. 19, 2018

(65) Prior Publication Data

US 2019/0184087 A1    Jun. 20, 2019

Related U.S. Application Data

(60) Provisional application No. 62/608,545, filed on Dec. 20, 2017.

(51) Int. Cl.
*A61M 1/36* (2006.01)
*B01D 17/02* (2006.01)
(Continued)

(52) U.S. Cl.
CPC ........ *A61M 1/3696* (2014.02); *A61M 1/0209* (2013.01); *A61M 1/3683* (2014.02);
(Continued)

(58) Field of Classification Search
CPC .............. A61M 1/3696; A61M 1/3693; A61M 1/0209; A61M 1/38; A61M 1/3681;
(Continued)

(56) References Cited

U.S. PATENT DOCUMENTS 5,360,542 A    11/1994    Williamson et al.
5,868,696 A    2/1999    Giesler et al.
(Continued)

FOREIGN PATENT DOCUMENTS

WO    1999003976 A2    1/1999

OTHER PUBLICATIONS

Florek.M., et al., Blood. 2014;124(11):1832-1842 "Autologous apoptotic ceils preceding transplantation enhance survivalin lethal murine graft-versus-host models".
Mevorach, D., et al., Biol Blood Marrow Transplant 20 (2014) 58e65, "Single Infusion of Donor Mononuclear Early Apoptotic Cellsas Prophylaxis for Graft-versus-Host Disease inMyeloablative HLA-Matched Allogeneic Bone Marrow Transplantation: A Phase I/IIa Clinical Trial".
(Continued)

*Primary Examiner* — Ariana Zimbouski
(74) *Attorney, Agent, or Firm* — Cook Alex Ltd.

(57) ABSTRACT

A method for prophylaxis or treatment of a graft's rejection of a recipient, driven and adjusted by a microprocessor-based controller. Provided is a fluid circuit comprising a first container configured to receive a transplant component and a second container configured to receive an apoptotic component. Provided is a separator configured to associate with the fluid circuit and separate whole blood into a red blood cell component, a plasma component, and a white blood cell component. Whole blood is directed into the fluid circuit and the separator. The whole blood is separated into the red blood cell component, the plasma component, and the white blood cell component. A first portion comprising the transplant component of the white blood cell component is directed to the first container. A second portion of the white blood cell component is directed to the second container and the second portion is rendered apoptotic.

7 Claims, 11 Drawing Sheets

(51) Int. Cl.
  *A61M 1/38*    (2006.01)
  *B04B 13/00*   (2006.01)
  *A61M 1/02*    (2006.01)
  *A61M 1/30*    (2006.01)

(52) U.S. Cl.
  CPC ............ *A61M 1/3693* (2013.01); *A61M 1/38* (2013.01); *B01D 17/0217* (2013.01); *B04B 13/00* (2013.01); *A61M 1/303* (2014.02); *A61M 2202/0439* (2013.01); *A61M 2205/053* (2013.01); *A61M 2205/3368* (2013.01); *B01D 2221/10* (2013.01)

(58) Field of Classification Search
  CPC ........ A61M 1/3683; A61M 2202/0439; B01D 17/0217; B04B 13/00
  See application file for complete search history.

(56) References Cited

U.S. PATENT DOCUMENTS

| | | | |
|---|---|---|---|
| 6,027,657 A | 2/2000 | Min et al. | |
| 7,433,030 B2 | 10/2008 | Waldo et al. | |
| 2008/0241815 A1 | 10/2008 | Edelson et al. | |
| 2009/0105683 A1* | 4/2009 | Spray | A61J 1/1475 264/240 |
| 2013/0197419 A1* | 8/2013 | Min | B04B 11/02 422/44 |

OTHER PUBLICATIONS

Peritt,D., Biology of Blood and Marrow i ransplantation 12:7-12 (2006), "Potential Mechanisms of Photopheresis in Hematopoietic Stem Ceil Transplantation".

* cited by examiner

SYSTEM AND METHOD OF COLLECTING AND INFUSING AN APOPTOTIC WHITE BLOOD CELL COMPONENT AND A TRANSPLANT COMPONENT

CROSS-REFERENCE TO RELATED APPLICATIONS

This application claims the benefit of U.S. Provisional Patent App. No. 62/608,545 filed Dec. 20, 2017, which is expressly incorporated herein by reference in its entirety.

FIELD OF THE DISCLOSURE

The present disclosure relates generally to systems and methods for collecting and infusing an apoptotic white blood cell component and a transplant component to a transplant recipient and, in particular to systems and methods for prophylaxis or treatment of a graft's rejection of a recipient or a recipient's rejection of a graft.

BACKGROUND

Whole blood is made up of various cellular and non-cellular components such as red cells, white cells and platelets suspended in its liquid component, plasma. Whole blood may be separated into its constituent components (cellular, liquid or other), and the separated component(s) may be administered to a patient in need of that particular component or components.

The administration of blood and/or blood components is common in the treatment of patients suffering from disease. Rather than infuse whole blood, individual components may be administered to the patient(s) as their needs require. For example, administration (infusion) of platelets may often be prescribed for cancer patients whose ability to make platelets has been compromised by chemotherapy. Infusion of white blood cells (e.g., mononuclear cells) after the cells have undergone some additional processing or treatment may also be prescribed for therapeutic reasons, including treatment of diseases that specifically involve the white blood cells. Thus, it may be desirable to separate and collect the desired blood component from whole blood and then treat the patient with the specific blood component. The remaining components may be returned to the patient or retained for other uses.

There are several diseases or disorders which are believed to primarily involve mononuclear cells, such as cutaneous T-cell lymphoma, organ allograft rejection after transplantation, and autoimmune diseases such as rheumatoid arthritis and systemic sclerosis, among others.

Cutaneous T-cell lymphoma (CTCL) is a term that is used to describe a wide variety of disorders. Generally, CTCL is a type of cancer of the immune system where T-cells (a type of mononuclear cell) mutate or grow in an uncontrolled way, migrate to the skin and form itchy, scaly plaques or patches. More advanced stages of the disease also affect the lymph nodes. Therapeutic treatment options for CTCL have previously been limited. While chemotherapy has been utilized, this particular form of treatment also has many associated undesirable side effects, such as lowered resistance to infection, bleeding, bruising, nausea, infertility and hair loss, just to name a few.

Organ allograft rejection may be characterized as the rejection of tissues that are foreign to a host, including transplanted cardiac tissue as well as lung, liver and renal transplants. Immunosuppression drug therapy following transplantation is common. However, there are potential drawbacks including reoccurring infection due to the compromised competence of the immune system caused by this type of therapy.

Similarly, graft versus host disease (GvHD) is a complication that can occur after a stem cell or bone marrow transplant in which the newly transplanted material attacks the transplant recipient's body. The differences between the donor's cells and recipient's tissues often cause T-cells from the donor to recognize the recipient's body tissues as foreign, thereby causing the newly transplanted cells to attack the recipient. GvHD may complicate stem cell or bone marrow transplantation, thereby potentially limiting these life-saving therapies. Therefore, after a transplant, the recipient may be administered a drug that suppresses the immune system, which helps reduce the chances or severity of GvHD.

SUMMARY

According to an exemplary embodiment, the present disclosure is directed to a method for prophylaxis or treatment of a graft's rejection of a recipient, at least partially driven and adjusted by a microprocessor-based controller. Provided is a disposable fluid circuit comprising a first product container configured to receive a transplant component and a second product container configured to receive an apoptotic component. Provided is a separator configured to associate with the disposable fluid circuit, the separator comprising a chamber configured to rotate about a rotational axis and convey whole blood into an inlet region of the chamber for separation into a red blood cell component, a plasma component, and a white blood cell component. Whole blood from a blood source is directed into the disposable fluid circuit and the separator. The whole blood is separated into the red blood cell component, the plasma component, and the white blood cell component. A first portion comprising the transplant component of the white blood cell component is directed to the first product container. A second portion of the white blood cell component is directed to the second product container and the second portion is rendered apoptotic.

According to an exemplary embodiment, the present disclosure is directed to a system for prophylaxis or treatment of a graft's rejection of a recipient. A donor disposable fluid circuit is in communication with a first product container configured to receive a transplant component. The donor disposable fluid circuit is also in communication with a second product container configured to receive an apoptotic component. A separator is configured to associate with the donor disposable fluid circuit. The separator comprises a chamber configured to rotate about a rotational axis and convey whole blood into an inlet region of the chamber for separation into a red blood cell component, a plasma component, and a white blood cell component. A microprocessor-based controller is in communication with the separator. The controller is configured to direct whole blood from a blood source into the donor disposable fluid circuit and the separator. The whole blood is separated into the red blood cell component, the plasma component, and the white blood cell component. A first portion comprising the transplant component of the white blood cell component is directed to the first product container. A second portion of the white blood cell component is directed to the second product container. The second product container comprising the second portion of the white blood cell component and a photoactivation agent is irradiated to create an apoptotic white blood cell component. A recipient disposable circuit is configured to receive the transplant component from the first product container and the apoptotic white blood cell component from the second container to be infused to a recipient.

According to an exemplary embodiment, the present disclosure is directed to a system for prophylaxis or treatment of a graft's rejection of a recipient or a recipient's rejection of a graft. A donor disposable fluid circuit is in communication with a transplant product container configured to receive a transplant component. A recipient disposable fluid circuit is in communication with a recipient product container configured to receive an apoptotic component. A separator is configured to associate with the donor disposable fluid circuit and the recipient disposable circuit. The separator comprises a chamber configured to rotate about a rotational axis and convey whole blood into an inlet region of the chamber for separation into a red blood cell component, a plasma component, and a white blood cell component. A microprocessor-based controller is in communication with the separator. The controller is configured to direct donor whole blood from a donor into the donor disposable fluid circuit and the separator. A donor white blood cell component comprising the transplant component is separated from remaining blood components. The transplant component is directed to the transplant product container. Recipient whole blood is directed from a recipient into the recipient disposable fluid circuit and the separator. The recipient whole blood is separated into a recipient red blood cell component, a recipient plasma component, and a recipient white blood cell component. The recipient white blood cell component is directed to the recipient product container. The recipient product container comprising the recipient white blood cell component and a photoactivation agent is irradiated to create an apoptotic white blood cell component. The apoptotic white blood cell component from the recipient product container is infused into the recipient disposable circuit to the recipient.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

DETAILED DESCRIPTION

Figure 1:
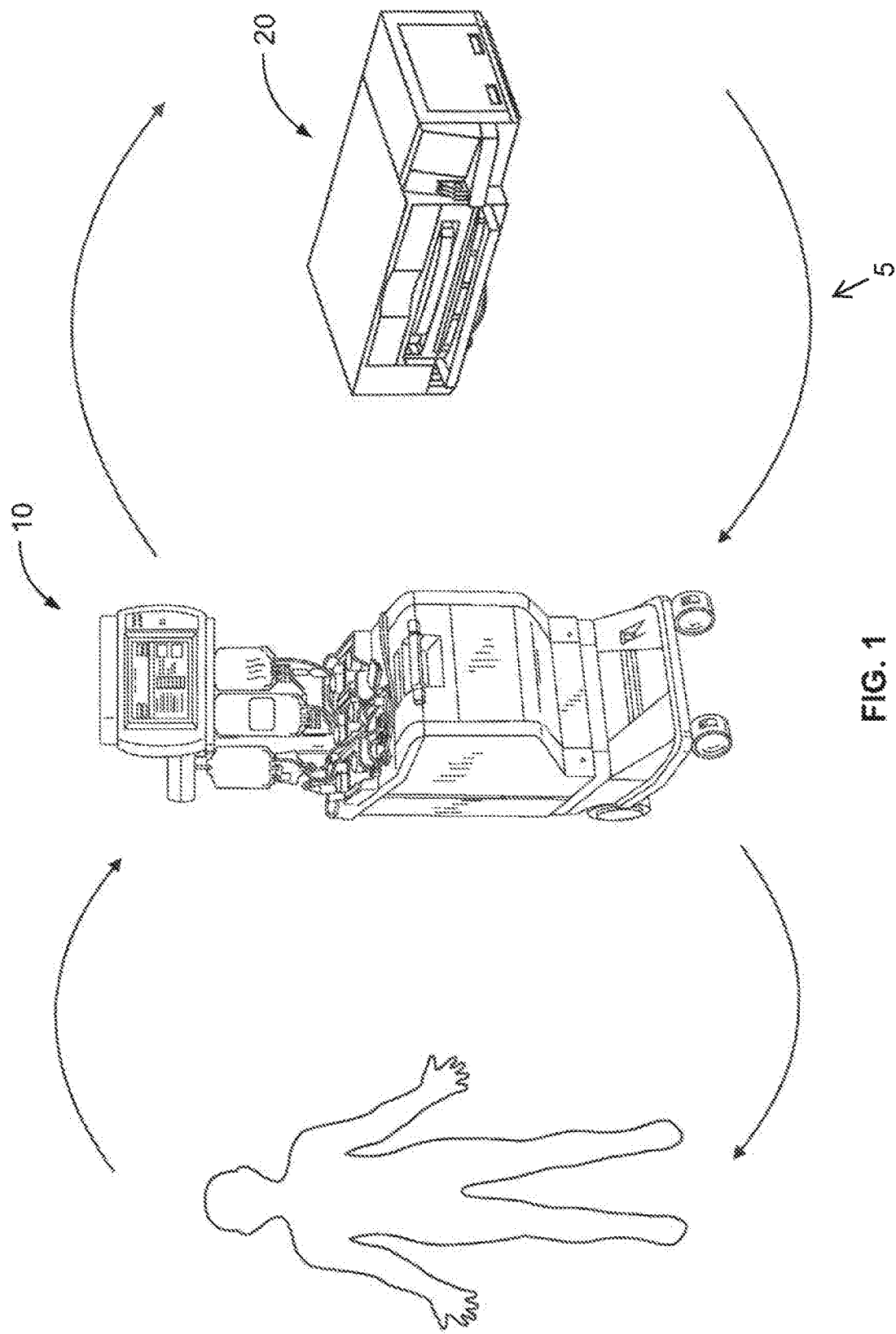
FIG. 1 is a diagram generally showing mechanical components of a photopheresis treatment device, according to an exemplary embodiment.

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

Where existing therapies for treating one or more diseases may result in certain unintended side effects, additional treatment may be desired or required. One procedure which has been shown to be effective in the treatment of diseases and/or the side effects of existing therapies involving mononuclear cells is extracorporeal photopheresis or "ECP". Extracorporeal photopheresis (also sometimes referred to as extracorporeal photochemotherapy) is a process that includes: (1) collection of mononuclear cells (MNC) from a blood source (e.g., patient, donor, blood container, etc.), (2) photoactivation treatment of the collected MNC cells; and (3) re-infusion of the treated cells (MNC) back to the blood source. More specifically, ECP involves the extracorporeal exposure of peripheral blood mononuclear cells combined with a photoactive compound, such as 8-methoxypsoralen or "8-MOP" which is then photoactivated by ultraviolet light, followed by the re-infusion of the treated mononuclear cells. The combination of 8-MOP and UV radiation may cause apoptosis or programmed cell death of ECP-treated T-cells.

During ECP treatment, photoactivation is known to cause 8-MOP to irreversibly covalently bind to the DNA strands contained in the T-cell nucleus. When the photochemically damaged T-cells are reinfused, cytotoxic effects may be induced. For example, a cytotoxic T-cell or "CD8+ cell" releases cytotoxins when exposed to infected or damaged cells or otherwise attacks cells carrying certain foreign or abnormal molecules on their surfaces. The cytotoxins target the damaged cell's membrane and enter the target cell, which eventually leads to apoptosis or programmed cell death of the targeted cell. In other words, after the treated mononuclear cells are returned to the body, the immune system recognizes the dying abnormal cells and begins to produce healthy lymphocytes (T-cells) to fight against those cells.

Alternatively, ECP may result in an immune tolerant response in different disease states. For example, in the case of graft versus-host disease, the infusion of apoptotic cells may stimulate regulatory T-cell generation, inhibit inflammatory cytokine production, cause the deletion of effective T-cells and result in other responses. See Peritt, "Potential Mechanisms of Photopheresis in Hematopoietic Stem Cell Transplantation," Biology of Blood and Marrow Transplantation 12:7-12 (2006). In another example, in the case of a graft or organ rejection (e.g., transplant rejection), the infusion of apoptotic cells originating from a donor, recipient, and/or third party prior to, in conjunction with, or after a graft or transplant may induce immune tolerance between a graft/transplant recipient and the graft/transplant. See Mevorach D., et al., "Single Infusion of Donor Mononuclear Early Apoptotic Cells as Prophylaxis for Graft-Versus-Host Disease in Myeloablative HLA-Matched Allogeneic Bone Marrow Transplantation: A Phase I/IIa Clinical Trial," Biology of Blood Marrow Transplantation 20(1):58-65 (2014) and Florek M., et al., "Autologous apoptotic cells preceding transplantation enhance survival in lethal murine graft-versus-host models," Blood 124(11)1832-1842 (2014).

In some embodiments, infusion of apoptotic leukocytes from the same donor as the stem cell or transplant source may help to prevent GvHD or organ rejection occurrences within the recipient post-transplantation.

In some embodiments, infusion of apoptotic leukocytes from a third party HLA-compatible donor different from the stem cell or transplant source and different from the recipient may help to prevent GvHD or organ rejection occurrences within the recipient post-transplantation.

In some embodiments, infusion of apoptotic leukocytes from the recipient may help to prevent GvHD or organ rejection occurrences within the recipient after receiving a stem cell or transplant from an allogeneic donor.

Some embodiments may save time and resources in collecting cells for GvHD prophylaxis and transplant by collecting donor apoptotic cells and cells to be transplanted within the same procedure.

Some embodiments may allow more efficient transplant cell collection from a mobilized donor having an elevated white blood cell (WBC) count and increase collection and treatment yield compared to non-mobilized collections.

Some embodiments may allow a device operator to select which fluid components remaining in a fluid circuit to return to a blood source, e.g., treated target cells, non-target cells, plasma, and/or not returning any fluid component to the blood source.

Figure 2:
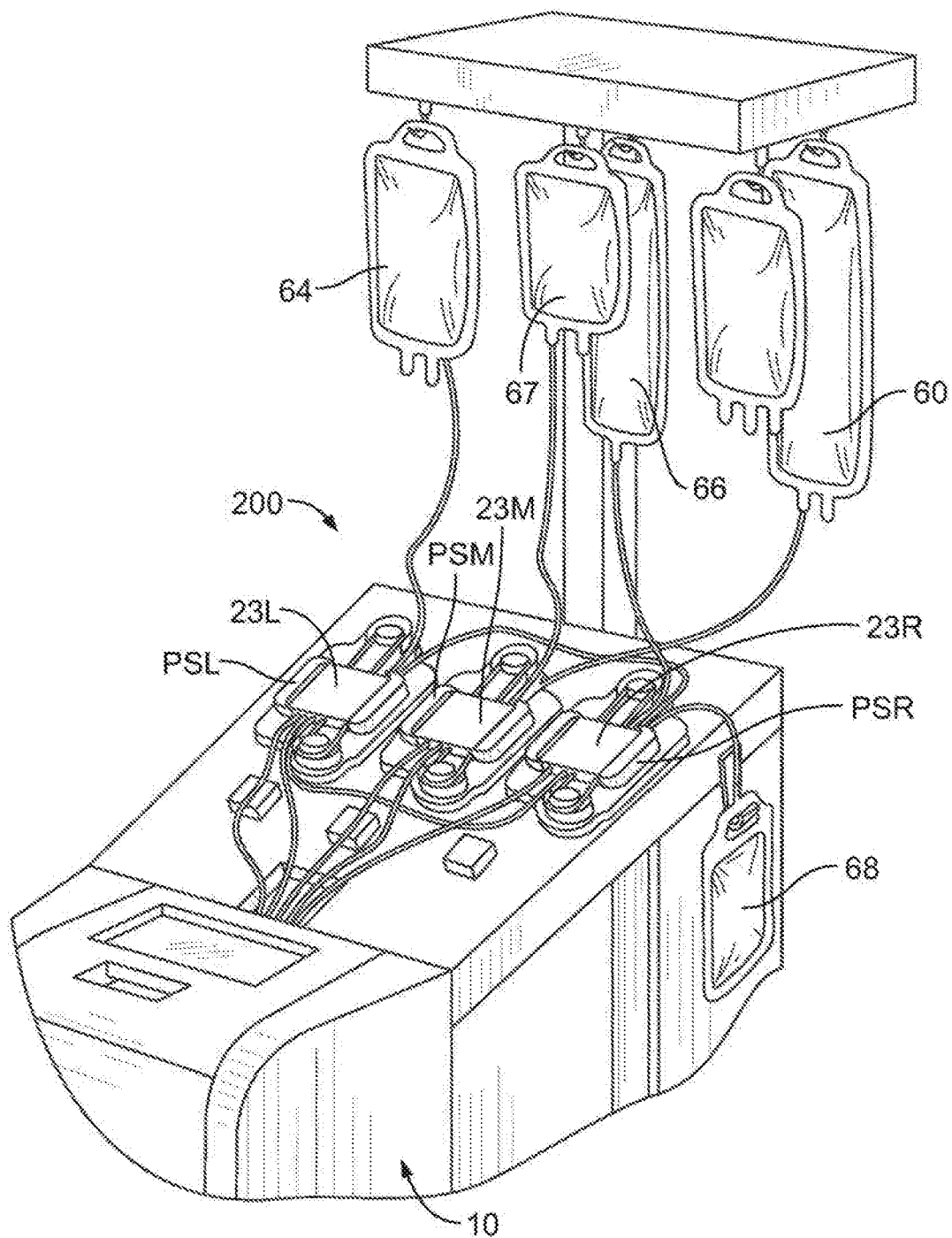
FIG. 2 is a partial perspective view of an apheresis separator useful in the methods and systems described herein, according to an exemplary embodiment.
Figure 4:
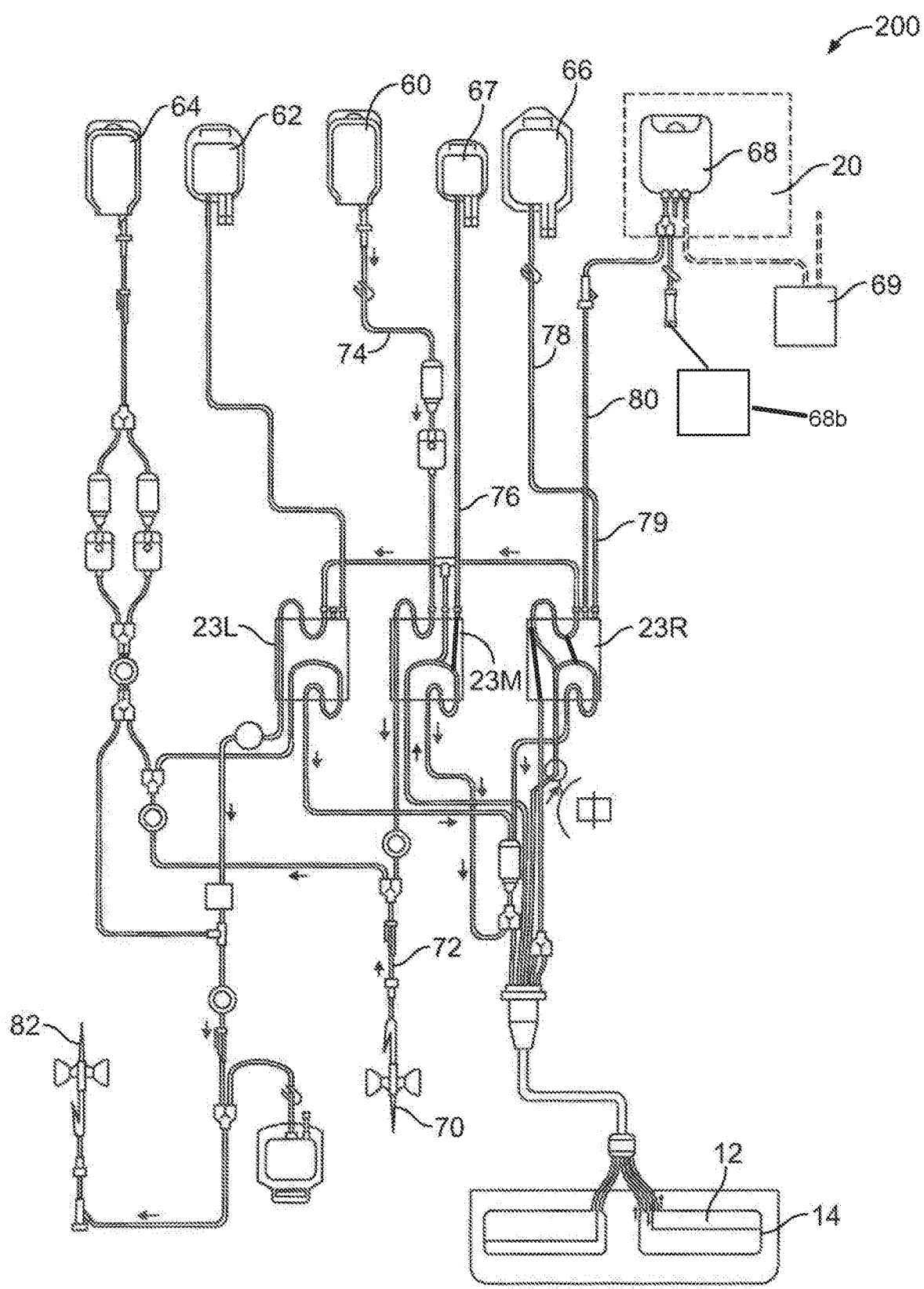
FIG. 4 is a diagram of a fluid circuit useful in the collection, treatment and infusion of target cells, according to an exemplary embodiment.

FIG. 1 shows, in general, the mechanical components that make up an ECP system 5 and that may be used in one or more of the systems and methods described herein to induce apoptosis of WBCs. The system 5 may include a separation component 10 and a treatment (i.e., irradiation) component 20. Irradiation component 20 may be independent and housed separately from the separation component 10, or components 20 and 10 may be integrated into a single device. In an embodiment in which components 20 and 10 are housed separately, the separation device 10 and irradiation device 20 may be located adjacent to each other, allowing an operator or clinician to have access to both devices during a particular treatment procedure. A blood source may be connected to a fluid circuit 200 as shown in FIGS. 1, 2, 4 that provides a sterile closed pathway between separation component 10 and irradiation component 20 and may be cooperatively mounted on the hardware of the separation device 10. The separation device 10 may have one or more features of an apheresis device, such as a system marketed as the AMICUS® separator by Fenwal, Inc. of Lake Zurich, Ill., as described in greater detail in U.S. Pat. No. 5,868,696, which is hereby incorporated herein by reference in its entirety, although any suitable separation device may be used.

With reference to FIG. 1, whole blood may be withdrawn from the blood source (e.g., donor, patient, recipient, etc.) and introduced into the separation component 10 where the whole blood is separated to provide a target cell population. In one embodiment, the target cell population may be mononuclear cells (MNCs) or MNCs of a particular type (lymphocytes, monocytes, stem cells, and/or dendritic cells, etc.). Other components separated from the whole blood, such as red blood cells (RBCs), plasma, and/or platelets may be returned to the blood source or collected in pre-attached containers of the blood processing set.

The separated target cell population, e.g., mononuclear cells, may then be treated and irradiated in treatment component 20. As discussed above, treatment of mononuclear cells may involve the photoactivation of a photoactive agent that has been combined with the mononuclear cells. Mononuclear cell collection, harvest, and transfer using a device such as the Amicus® are described in greater detail in U.S. Pat. No. 6,027,657, the contents of which are incorporated by reference herein in its entirety. Preferably, the apparatus used for the harvesting, collection and reinfusion of mononuclear cells may be a "multifunctional" automated apheresis device, as is the case with the Amicus® Separator. In other words, the separation component 10 may be a multifunctional automated apparatus that can perform various collection protocols and/or serve multiple purposes, as may be needed by a particular hospital or facility, such that it can be used not only in the systems and methods for performing photopheresis treatment of MNC as described herein, but can also be used for other purposes including the collection of blood and blood components including platelets, plasma, red blood cells, granulocytes and/or perform plasma/RBC exchange, among other functions required by the hospital or medical facility.

Figure 3:
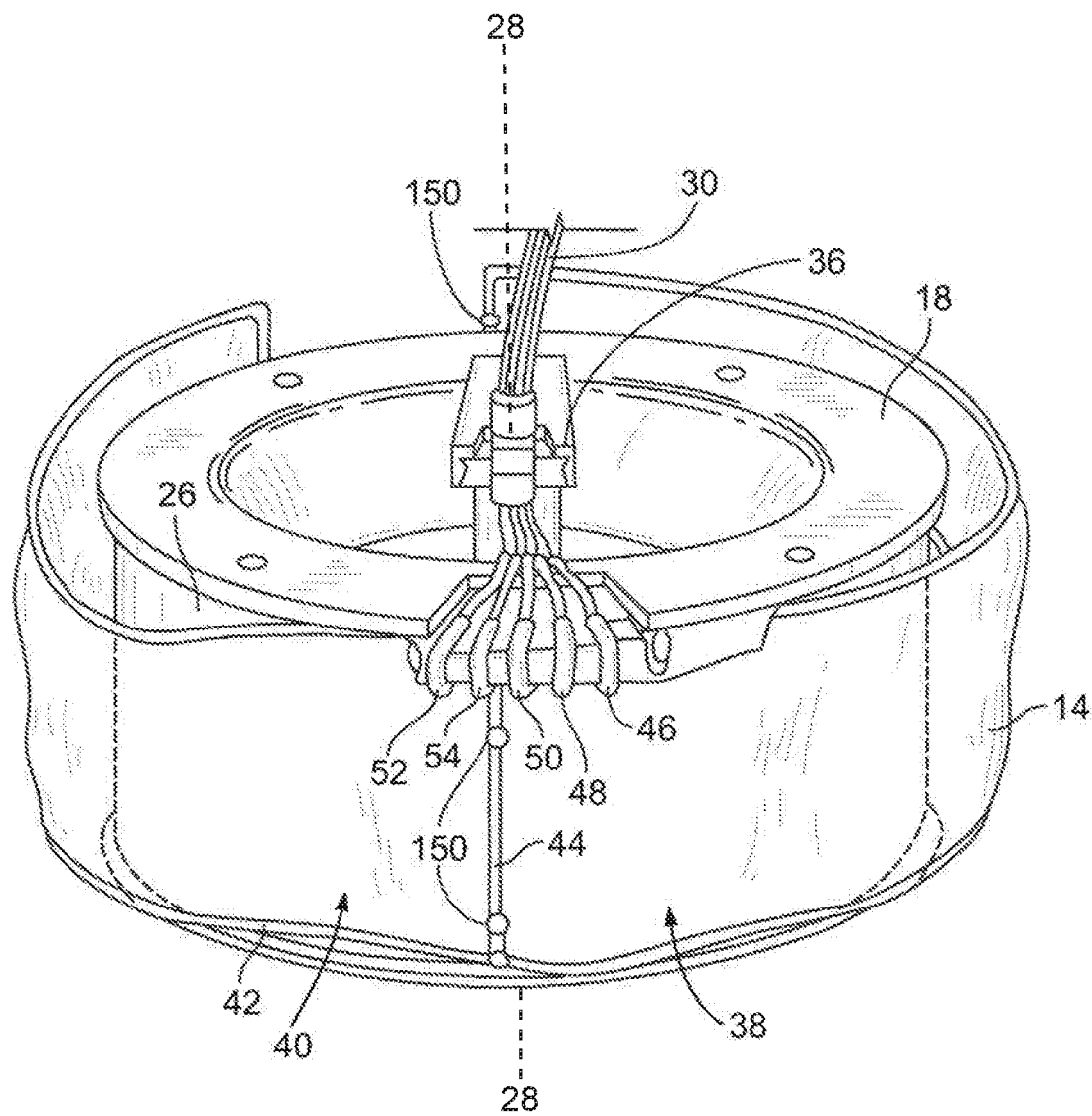
FIG. 3 is a perspective view of a separation chamber of the processing set used with the separator of FIG. 2, according to an exemplary embodiment.

FIGS. 2-4 depict a separator 10 with fluid circuit 200 mounted thereon (FIG. 2), the fluid circuit (FIG. 4) having a blood processing container 14 (FIG. 3) defining a separation chamber 12 suitable for harvesting mononuclear cells (MNC) from whole blood. As shown in FIG. 2, a disposable processing set or fluid circuit 200 (which includes container 14) may be mounted on the front panel of separator 10. The fluid circuit 200 may include a plurality of processing cassettes 23L, 23M and 23R with tubing loops for association with peristaltic pumps on separator 10. Fluid circuit 200 may also include a network of tubing and pre-connected containers for establishing flow communication with the blood source and for processing and collecting fluids and blood and blood components, as shown in FIG. 4. As seen in FIGS. 2 and 4, disposable processing set 200 may include a container 60 for supplying anticoagulant, a waste container 62 for collecting waste from one or more steps in the process for treating and washing mononuclear cells, a container 64 for holding saline or other wash or resuspension medium, a container 66 for collecting plasma, a container 68 for collecting the mononuclear cells and, optionally, container 69 for holding the photoactivation agent.

Container 68 may also serve as the illumination container, and the illumination container 68 may be pre-attached to and integral with the disposable set 200. Alternatively, container 68 may be attached to set 200 by known sterile connection techniques, such as sterile docking or the like. In FIG. 2, container 68 is shown as suspended from device 10. However, container 68 may be housed within an adjacent separately housed irradiation device 20 (as shown by broken lines in FIG. 4), thereby eliminating the step of having the operator place container 68 into irradiation device 20. The tubing leading to and/or from container 68 in fluid circuit 200 may be of a sufficient length to reach an irradiation device 20 that is adjacent to but housed separately from the separation device.

With reference to FIG. 4, fluid circuit 200 may include inlet line 72, an anticoagulant (AC) line 74 for delivering AC from container 60, an RBC line 76 for conveying red blood cells from chamber 12 of container 14 to container 67, a platelet poor plasma (PPP) line 78 for conveying PPP to container 66 and line 80 for conveying mononuclear cells to and from blood processing container 14 and collection/illumination container 68. The blood processing set may include one or more access device(s) (e.g., venipuncture needle, adapter, connector) for accessing the blood source (e.g., circulatory system of a patient, blood-filled bag). As shown in FIG. 4, fluid circuit 200 may include inlet access device 70 and return access device 82. In an alternative embodiment, a single access device may serve as both the inlet and outlet access device.

Fluid flow through fluid circuit 200 may be driven, controlled and adjusted by a microprocessor-based controller in cooperation with the valves, pumps, weight scales and sensors of device 10 and fluid circuit 200, the details of which are described in the aforementioned U.S. Pat. No. 6,027,657, although any suitable controller may be used.

In accordance with the present disclosure, the fluid circuit may be further adapted for association with the irradiation device 20. One example of a suitable irradiation device is described in U.S. Pat. No. 7,433,030, which is incorporated by reference herein in its entirety, although any suitable irradiation device may be used. The irradiation device 20 may include a tray or other holder for receiving one or more containers during treatment.

Referring to FIG. 3, separation chamber 12 is defined by the walls of a flexible processing container 14 carried within an annular gap defined by a rotating spool element 18 and an outer bowl element (not shown). The blood processing container 14 may take the form of an elongated tube which is wrapped about the spool element 18 before use. The bowl and spool element 18 may be pivoted on a yoke between an upright position and a suspended position. In operation, the centrifuge 10 may rotate the suspended bowl and spool element 18 about an axis 28, creating a centrifugal field within the processing container 14. Details of the mechanism for causing relative movement of the spool 18 and bowl elements as described are disclosed in U.S. Pat. No. 5,360,542 entitled "Centrifuge with Separable Bowl and Spool Elements Providing Access to the Separation Chamber," which is also incorporated herein by reference in its entirety, although any suitable separation mechanism may be used.

Figure 5:
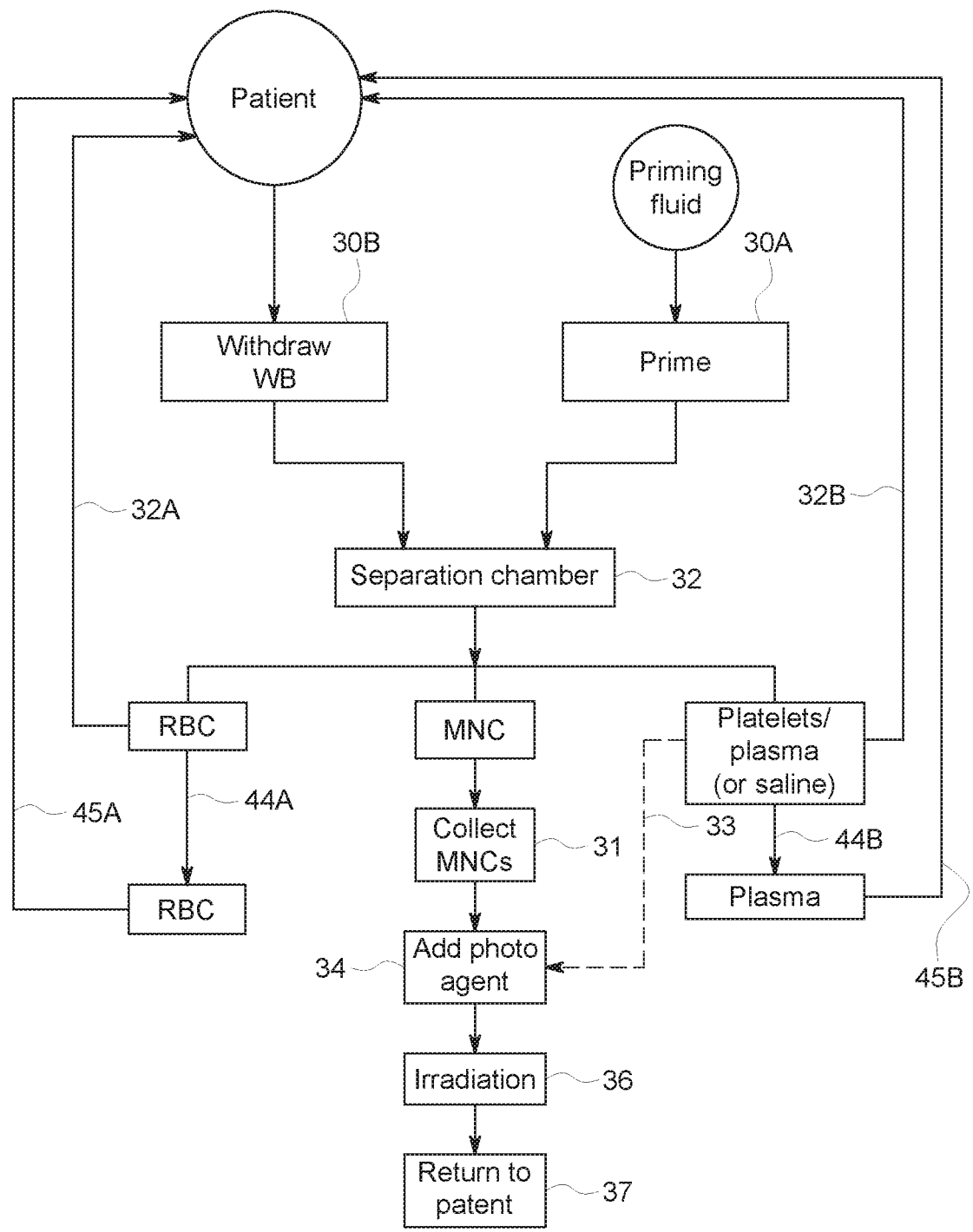
FIG. 5 is a flow chart setting forth steps of a method of an online photopheresis treatment, according to an exemplary embodiment.

FIG. 5 depicts one embodiment of an online method of treating mononuclear cells. An "online" photopheresis system includes both the blood separation device and the irradiation device in an integrated system. An online system provides for reinfusion of treated target cells back to the blood source. The fluid circuit 200 of FIG. 4 may first be primed with a priming fluid, such as saline, albumin, and/or blood components (step 30A). Whole blood may then be withdrawn from a blood source (step 30B) through inlet access device 70 (FIG. 4) and introduced into the separation chamber 12 of container 14 of processing set 200, where the whole blood is subjected to a centrifugal field. The centrifugal field may separate the target cell population, i.e., mononuclear cells, from a red blood cell constituent and a platelet/plasma constituent (step 32). A portion of the components of red blood cells and platelets/plasma may be returned to the blood source (steps 32A and 32B). Another portion of red blood cells and platelets/plasma may be diverted to other portions of the fluid circuit 200 (e.g., container 67 for RBCs, container 66 for plasma/platelets) for further utilization and/or processing (steps 44A and 44B). Collection of the mononuclear cells may proceed in one or more cycles comprising steps 30B, 32, 32A, 32B, 44A, and 44B, with the number of processing cycles conducted in a given therapeutic procedure depending upon the total yield of MNCs to be collected and/or the desired volume of whole blood to be processed. Once the desired number of cycles has taken place, the MNCs accumulated in the separation chamber 12 may be collected (step 31). A photoactivation agent may be added to the collected MNCs (step 34), and the MNCs may be irradiated (step 36). The portion of red blood cells and platelets/plasma that were diverted to other portions of the fluid circuit 200 in steps 44A and 44B may be reinfused into the blood source (steps 45A and 45B) while the MNCs are being irradiated in step 36, or they may be reinfused during reinfusion of the irradiated MNCs into the blood source (step 37).

Although FIG. 5 depicts an online method of treating MNCs, offline methods are available as well. In offline methods, an apheresis device may be used to collect target cells. The collected target cells, typically contained in one or more collection containers, are severed or otherwise separated from the tubing set used during collection, where they are later treated in a separate irradiation or UVA light device followed by subsequent reinfusion of the treated cells to a blood source. During such offline methods, when the cells are transferred from the apheresis device to the irradiation device (which device may be located in another room or laboratory), communication with the blood source is severed and the cells detached from the blood source.

Effective treatment of the MNCs with light may be facilitated by collecting mononuclear cells in a suspension having a suitable hematocrit, volume, and/or thickness. The hematocrit, volume, and/or thickness of the MNC suspension to be treated may affect the amount of UV light absorbed by the MNCs, given that the red blood cells in the MNC suspension block at least a portion the UV light from reaching the targeted MNCs. Control of hematocrit may be desirable in cases in which the light source of the irradiation device is configured to irradiate a set intensity of light, limited settings of light intensity values, and/or a set dose of irradiation, although hematocrit/thickness control may be desirable also in cases in which intensity, dose, and/or exposure settings may readily be adjusted according to hematocrit. It is common for a transmitter (e.g., bank of light bulbs) of an irradiation device to not be adjustable in terms of intensity of emission and therefore may emit a near-constant intensity of light. If the hematocrit of the suspended MNCs is too high (such that the red blood cells prevent the absorption of light by the MNCs), it may be desired to dilute the mononuclear cells with a diluting solution, such as plasma or saline, as shown in step 33 (FIG. 5), to control the hematocrit, volume, and/or thickness so that a desired amount of UV light will reach the targeted MNC. The diluted mononuclear cells (in container 68) may then be combined with the suitable photoactivation agent in step 34.

Figure 6:
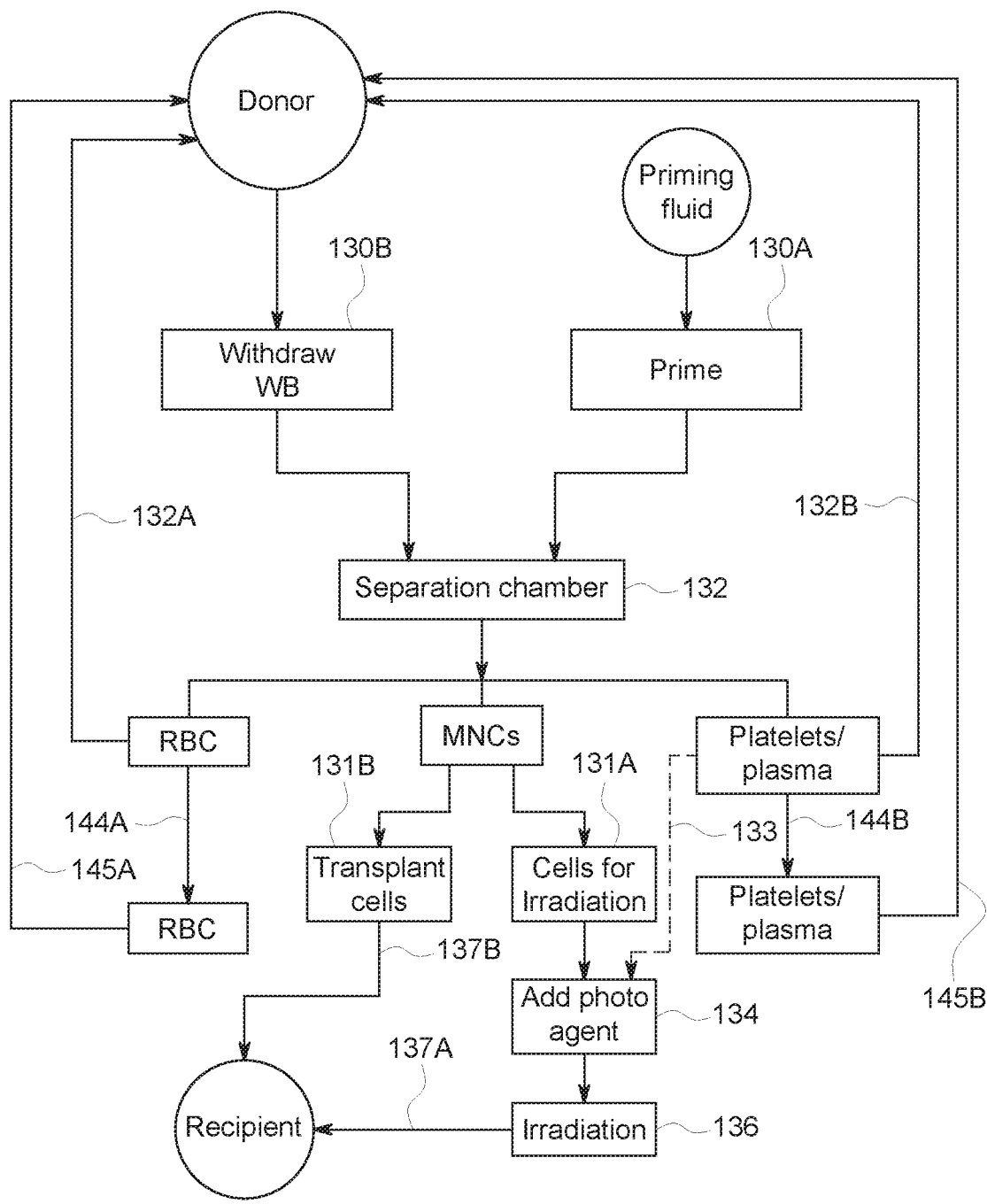
FIG. 6 is flow chart setting forth steps of a method of treatment in which a portion of the target cells are not returned to the blood source and returning remaining components in the fluid circuit, according to an exemplary embodiment.

FIG. 6 depicts an embodiment in which at least a portion of the target cells are not returned to the blood source while reinfusing the remaining blood components and other fluids remaining in the fluid circuit. It may be desirable not to return at least a portion of the target cells if the procedure is terminated for any reason, e.g., if a leak is detected in treatment container 68 (FIG. 4), a temperature threshold is exceeded, a UV sensor is out of range, donor blood volume is irregular, contamination risk is present, etc. It may also be desirable to collect rather than return at least a portion of the target cells in the event at least a portion of the target cells are intended for other purposes, e.g., transplantation, incubation. For example, a mobilized allogeneic donor with elevated white blood cells may donate, e.g., both MNCs to be irradiated and stem cells to be transplanted. The MNCs may be treated with 8-MOP and UVA light to render them apoptotic, while the stem cells may be untreated and used later for stem cell transplantation. In one embodiment, the treated MNCs from the donor may be infused into a recipient prior to transplanting the donor's untreated stem cells into the recipient in order to prevent GvHD post-transplantation.

At step 130A of FIG. 6, the fluid circuit 200 of FIG. 4 may first be primed with a priming fluid, e.g., saline, albumin, and/or blood components. Whole blood may then be withdrawn from a blood source (step 130B) through inlet access device 70 (FIG. 4) and introduced into the separation chamber 12 of container 14 of processing set 200, where the whole blood is subjected to a centrifugal field. The centrifugal field may separate the target cell population, e.g., mononuclear cells, from a red blood cell constituent and a platelet/plasma constituent (step 132). A portion of the components of red blood cells and platelets/plasma may be returned to the blood source (steps 132A and 132B) into whole blood. Another portion of red blood cells and platelets/plasma may be diverted (steps 144A and 144B) to other portions of the fluid circuit 200 (e.g., container 67 for RBCs, container 66 for plasma/platelets) for further utilization and/or processing. A portion of MNCs intended for apoptotic treatment may be collected (step 131A) into, e.g., container 68 of FIG. 4. Another portion of MNCs, e.g., stem cells intended for transplantation, may be collected at step 131B into, e.g., container 68b. A portion of plasma and/or saline may be added (step 133) to the MNCs intended for apoptotic treatment to achieve a desired hematocrit, volume, and/or thickness. Collection of the MNCs may proceed in one or more cycles comprising the steps 130B, 132, 132A, 132B, 144A, and 144B, with the number of processing cycles conducted in a given therapeutic procedure depending upon the total yield of MNCs to be collected and/or the desired volume of whole blood to be processed. Once the desired number of cycles has taken place, the MNCs accumulated in the separation chamber 12 may be collected (steps 131A and 131B). A photoactivation agent may be added (step 134) to the MNCs intended for apoptotic treatment collected in step 131A, and the MNCs may be irradiated (step 136). The portion of red blood cells and platelets/plasma that were diverted to other portions of the fluid circuit 200 in steps 144A and 144B may be reinfused into the blood source (steps 145A and 145B) while the MNCs are being irradiated in step 136.

In one embodiment, steps 131A, 134, and/or 136 taking place while MNCs intended for transplantation are still collecting within separation 12 may save additional time. In one embodiment, the donor may be disconnected from the fluid circuit 200 (FIG. 4) after steps 131A and 131B prior to irradiation (step 136). In one embodiment, MNCs intended for apoptotic treatment may be rendered apoptotic by methods other than photopheresis. For example, in lieu of steps 134 and 136, MNCs collected at step 131A may be subjected to temperature shocks (e.g., heat shocks, cool shocks), light therapy without the presence of a photoactivation agent, light treatments of alternate types (e.g., UVC), or gamma irradiation.

Once irradiation in step 136 of FIG. 6 is complete, the irradiated MNCs collected in container 68 of FIG. 4 intended for apoptotic treatment may be infused into a recipient (step 137A), and the transplant cells collected in container 68b intended for transplantation may be transplanted into the recipient (step 137B). In an embodiment in which steps 137A and/or 137B are to take place within a day of collection from the donor (steps 131A, 131B), the system 10 (FIG. 1) may prompt an operator to connect the recipient to the system 10 along with a different disposable circuit, which may be a circuit similar to the circuit 200 or may be an infusion circuit or kit that may be manually operated rather than in association with the system 10. In one embodiment in which GvHD prophylaxis is desired, apoptotic MNCs may be infused into a recipient (step 137A) as late as 3 days prior to transplantation of cells to the recipient (step 137B). In another embodiment in which GvHD prophylaxis is desired, apoptotic MNCs may be infused into a recipient (step 137A) as early as 10 days after step 137B prior to GvHD symptoms manifesting. In an embodiment in which GvHD treatment is desired (subsequent to manifestation of symptoms), apoptotic MNCs may be infused into a recipient (step 137A) as soon as symptoms manifest subsequent to transplantation. In embodiments in which the donated apoptotic cells and/or transplant cells are not infused within several days of donation to the recipient, the apoptotic cells and/or transplant cells may be cryopreserved until the time of infusion.

Figure 7:
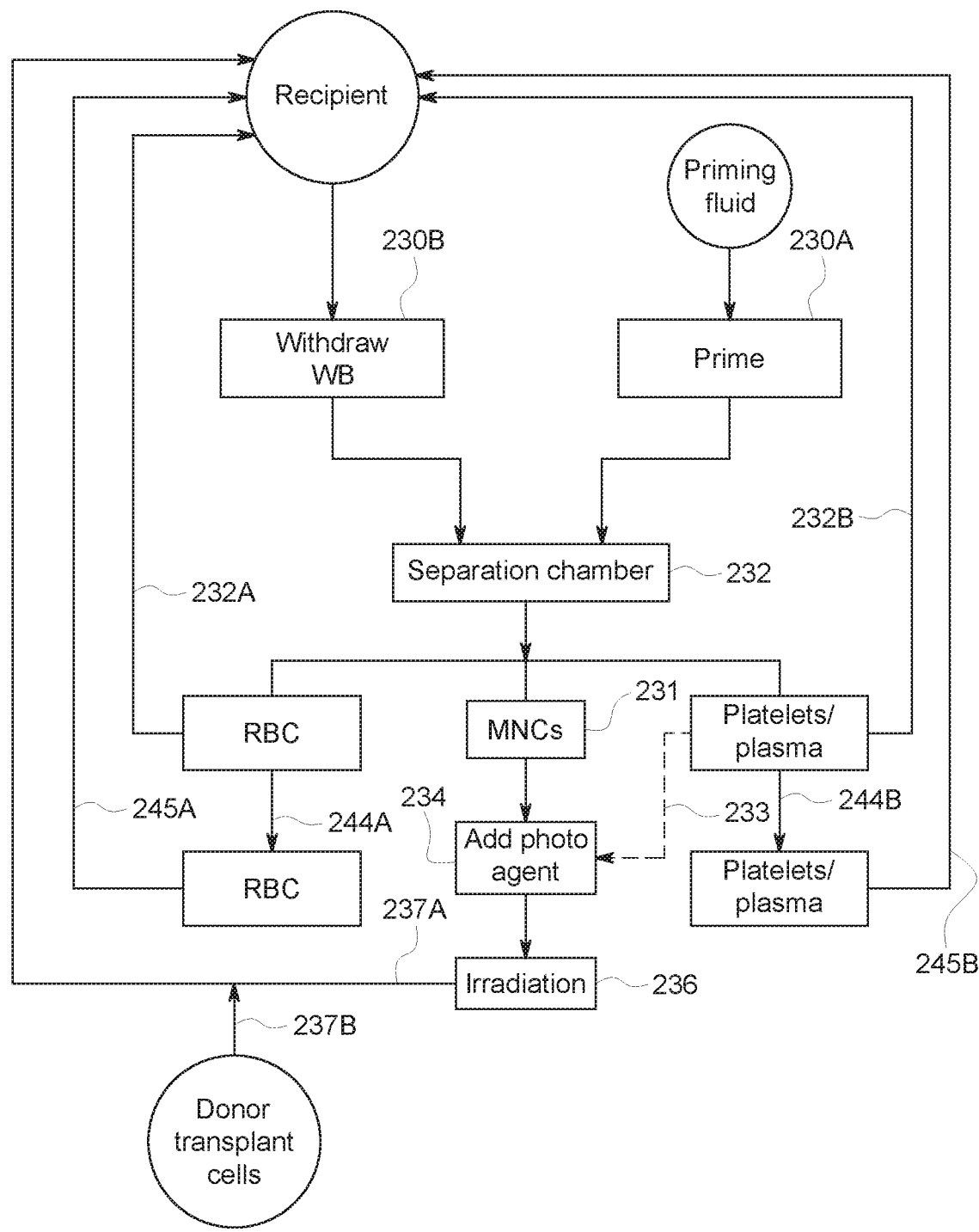
FIG. 7 is flow chart setting forth steps of a method in which apoptotic cells originating from a transplant recipient are used for GvHD prophylaxis or treatment, and an allogeneic donor's stem cells are used for transplantation, according to an exemplary embodiment.

FIG. 7 depicts an embodiment in which apoptotic cells originating from a transplant recipient are used for GvHD prophylaxis or treatment, while an allogeneic donor's stem cells are used for transplantation. The recipient's MNCs may be treated with 8-MOP and UVA light to render them apoptotic, while the donor's stem cells may be infused at an appropriate time relative to infusion of apoptotic cells. In one embodiment, the stem cells from the donor may be infused into the recipient subsequent to returning the recipient's apoptotic MNCs in order to prevent GvHD post-transplantation.

At step 230A of FIG. 7, the fluid circuit 200 of FIG. 4 may first be primed with a priming fluid, e.g., saline, albumin, and/or blood components. Whole blood may then be withdrawn from a blood source (step 230B) through inlet access device 70 (FIG. 4) and introduced into the separation chamber 12 of container 14 of processing set 200, where the whole blood is subjected to a centrifugal field. The centrifugal field may separate the target cell population, e.g., mononuclear cells, from a red blood cell constituent and a platelet/plasma constituent (step 232). A portion of the components of red blood cells and platelets/plasma may be returned to the blood source (steps 232A and 232B) into whole blood. Another portion of red blood cells and platelets/plasma may be diverted (steps 244A and 244B) to other portions of the fluid circuit 200 (e.g., container 67 for RBCs, container 66 for plasma/platelets) for further utilization and/or processing. MNCs intended for apoptotic treatment may be collected (step 231) into, e.g., container 68 of FIG. 4. A portion of plasma and/or saline may be added (step 233) to the MNCs intended for apoptotic treatment to achieve a desired hematocrit, volume, and/or thickness. Collection of the MNCs may proceed in one or more cycles comprising the steps 230B, 232, 232A, 232B, 244A, and 244B, with the number of processing cycles conducted in a given therapeutic procedure depending upon the total yield of MNCs to be collected and/or the desired volume of whole blood to be processed. Once the desired number of cycles has taken place, the MNCs accumulated in the separation chamber 12 may be collected (step 231). A photoactivation agent may be added (step 234) to the MNCs intended for apoptotic treatment collected in step 231, and the MNCs may be irradiated (step 236). The portion of red blood cells and platelets/plasma that were diverted to other portions of the fluid circuit 200 in steps 244A and 244B may be reinfused into the blood source (steps 245A and 245B) while the MNCs are being irradiated in step 236. In one embodiment, MNCs intended for apoptotic treatment may be rendered apoptotic by methods other than photopheresis. For example, in lieu of steps 234 and 236, MNCs collected at step 231 may be subjected to temperature shocks (e.g., heat shocks, cool shocks), light therapy without the presence of a photoactivation agent, light treatments of alternate types (e.g., UVC), or gamma irradiation.

Once irradiation in step 236 of FIG. 7 is complete, the apoptotic MNCs collected in container 68 of FIG. 4 may be infused into the recipient (step 237A), and the transplant cells donated by the allogeneic donor (e.g., contained in container 68b of FIG. 4) may be transplanted into the recipient (step 237B). In one embodiment in which GvHD prophylaxis is desired, the recipient's own apoptotic MNCs may be reinfused (step 237A) as late as 3 days prior to transplantation of cells to the recipient (step 237B). In another embodiment in which GvHD prophylaxis is desired, the apoptotic MNCs may be infused into the recipient (step 237A) as early as 10 days after step 237B prior to GvHD symptoms manifesting. In an embodiment in which GvHD treatment is desired (subsequent to manifestation of symptoms), apoptotic MNCs may be infused into the recipient (step 237A) as soon as symptoms manifest subsequent to transplantation. In embodiments in which the recipient's apoptotic cells are not infused within several days of donation (step 237B) to the recipient, the apoptotic cells and/or transplant cells may be cryopreserved until the time of infusion (step 237A).

FIGS. 8A-8D illustrate exemplary embodiments of fluid flow paths within the fluid circuit 200 of FIG. 4 when at least a portion of the target cells are not returned to the blood source while reinfusing the remaining blood components and other fluids remaining in the fluid circuit. As stated previously in reference to FIG. 6, it may be desirable not to return at least a portion of the target cells if the procedure is terminated and/or at least a portion of the target cells are intended for other purposes.

Figure 8A:
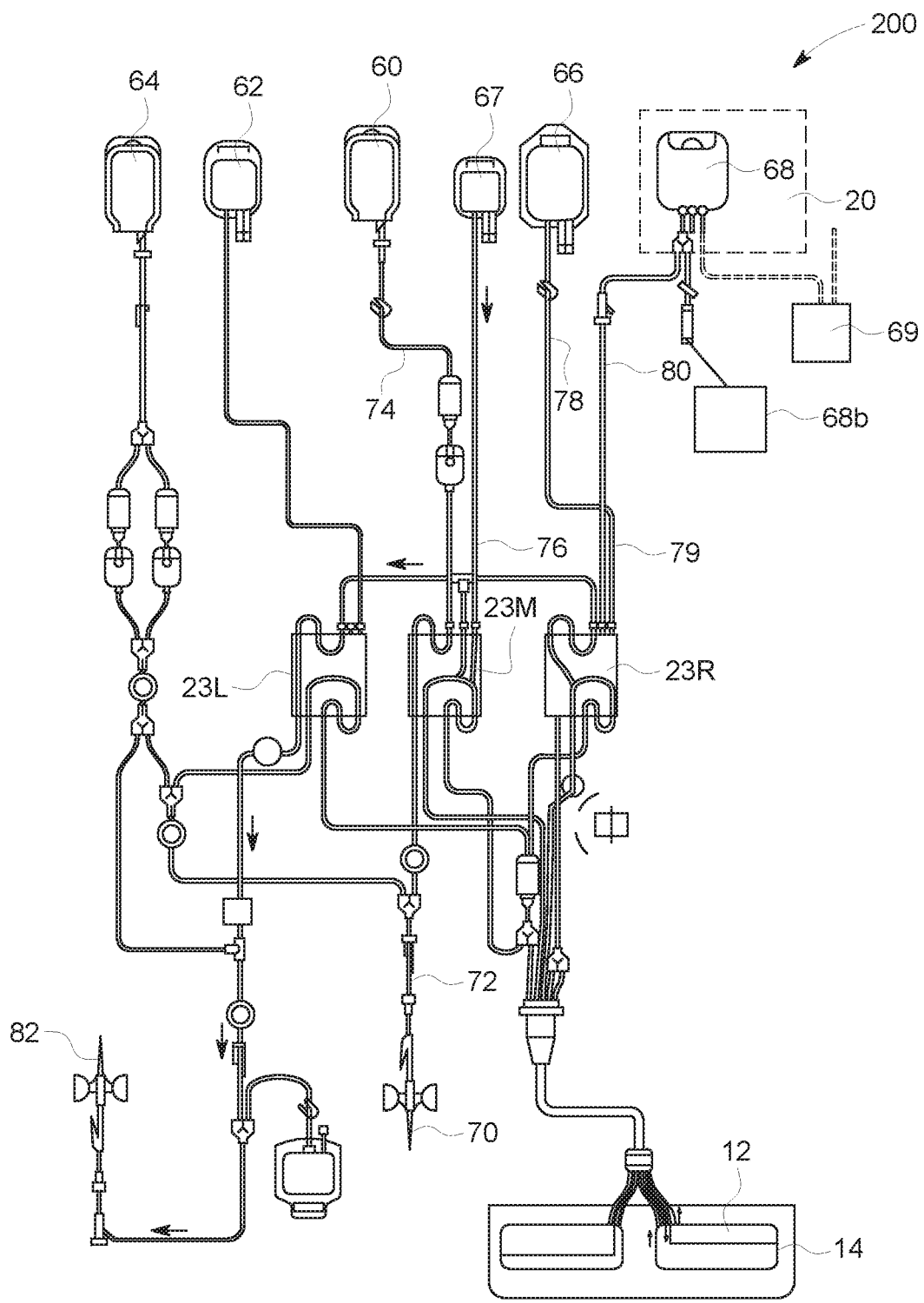
FIGS. 8A-8D are diagrams of fluid flow paths when a portion of the target cells are not returned to the blood source and remaining components in the fluid circuit are returned, according to an exemplary embodiment.
Figure 8B:
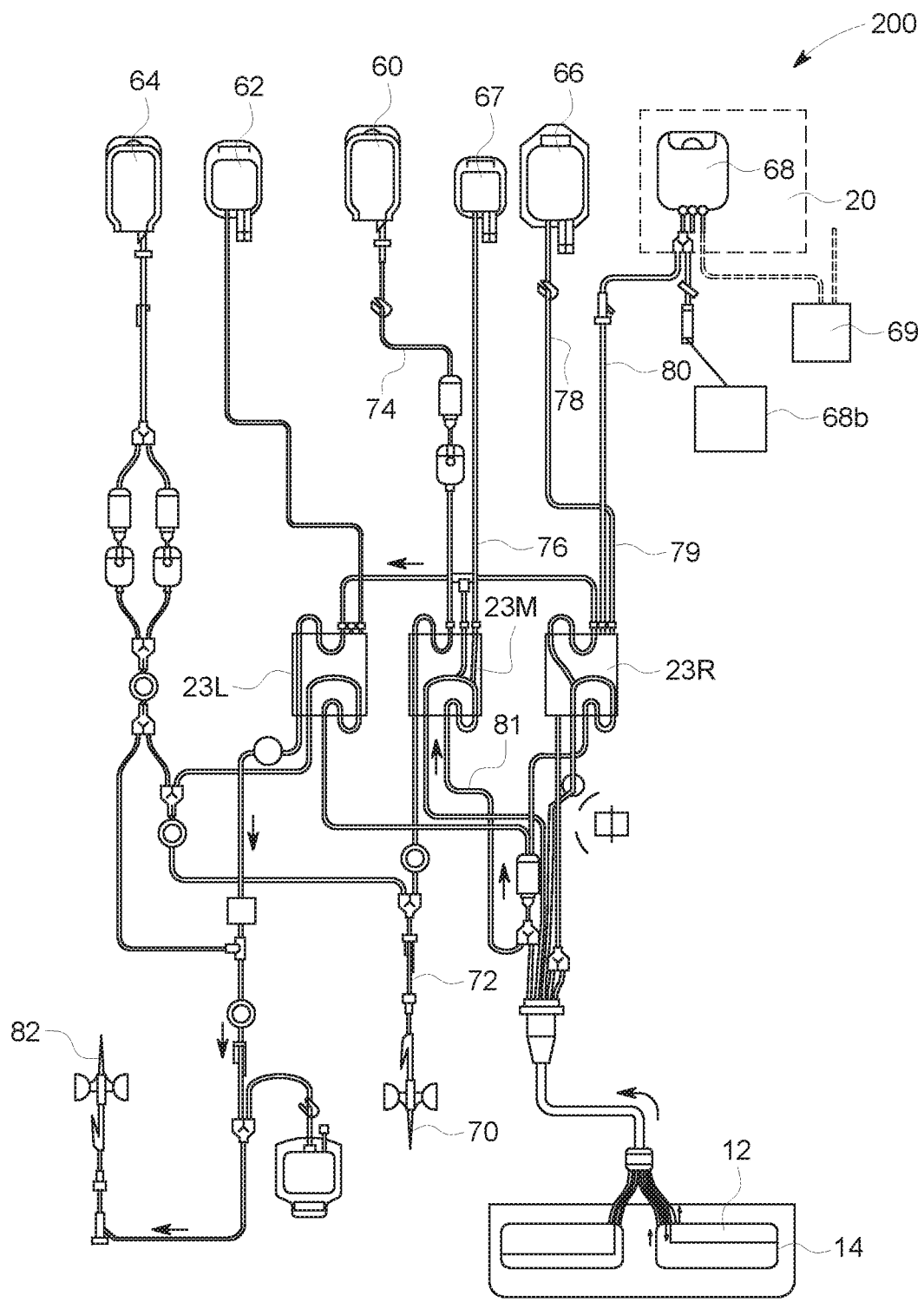
Figure 8C:
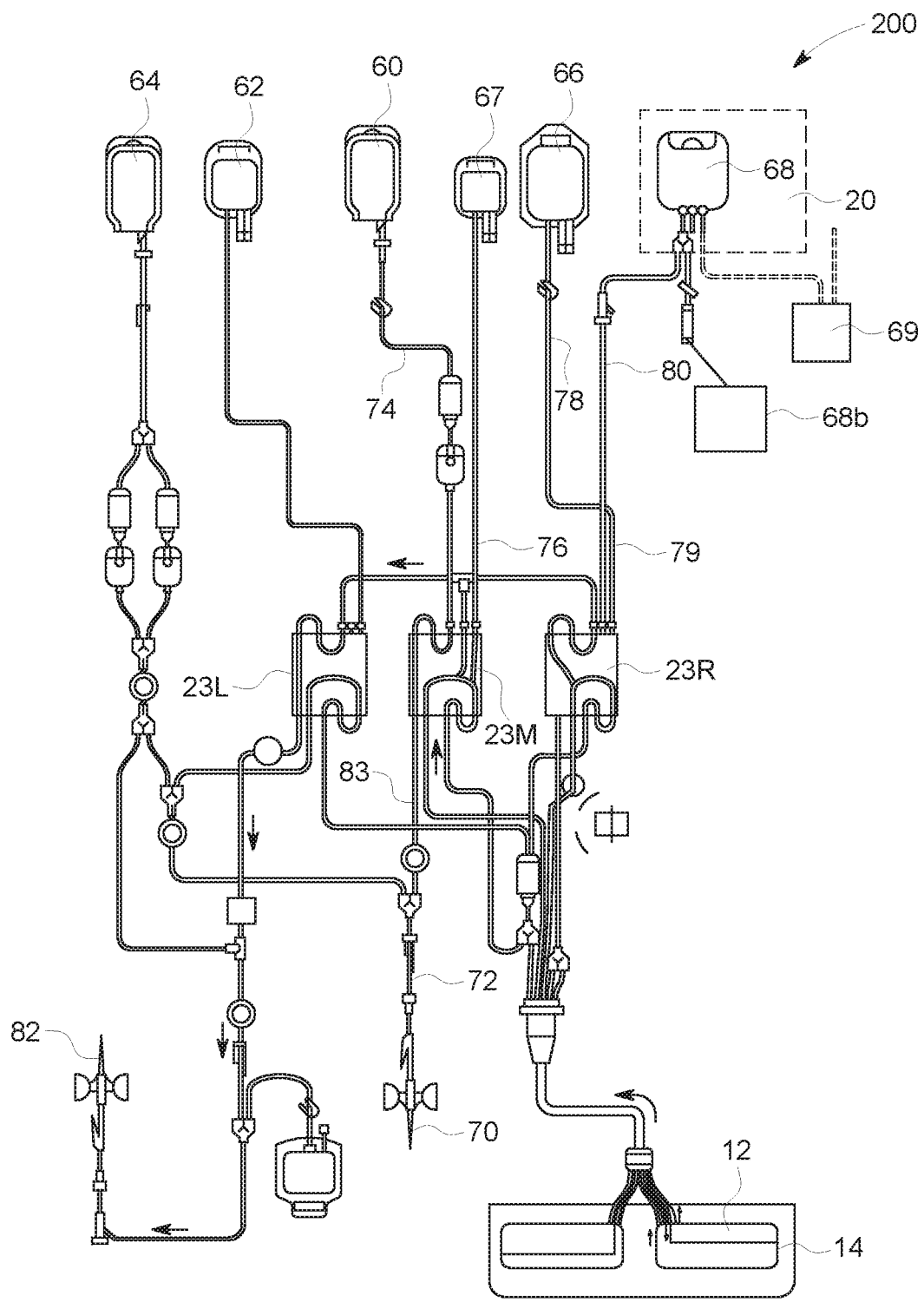
Figure 8D:
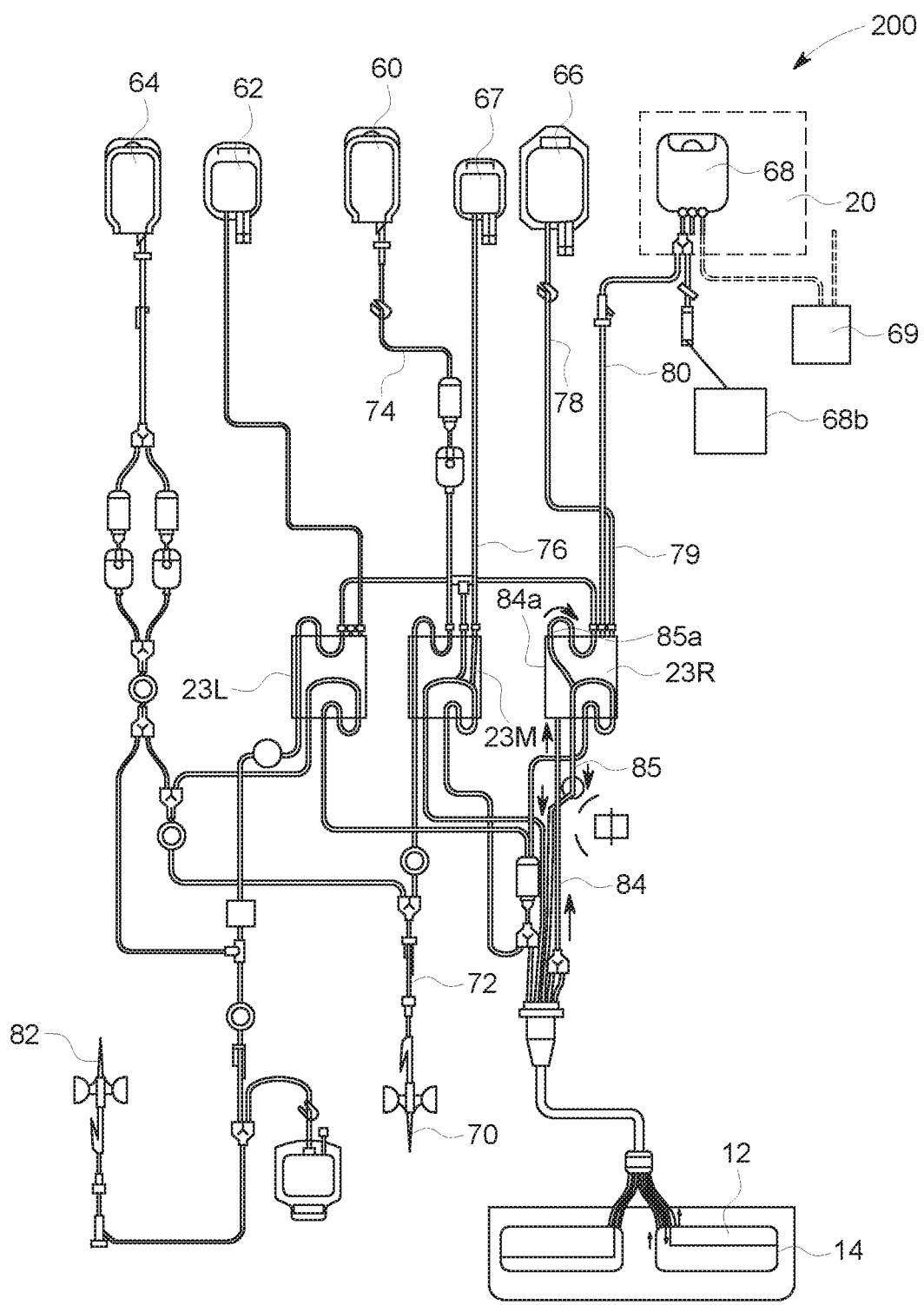

FIG. 8A depicts one embodiment of a fluid flow path for returning RBCs to the blood source (step 145A of FIG. 6). RBCs directed to container 67 during step 144A may be pumped via cassette 23M into cassette 23L and back to the blood source via return access device 82. FIG. 8B depicts one embodiment of a fluid flow path for then returning whole blood from the separation chamber 12 (FIG. 4) to the blood source. Whole blood within the separation 12 may include RBCs, plasma, platelets, and/or any MNCs not separated from the whole blood. Whole blood from chamber 12 may be pumped into tubing 81 via cassette 23M into cassette 23L and back to the blood source via return access device 82. FIG. 8C depicts one embodiment of a fluid flow path for then returning whole blood from the separation chamber 12 (FIG. 4) to the blood source via an alternate pathway. Whole blood from chamber 12 may be pumped into tubing 83 via cassette 23M into cassette 23L and back to the blood source via return access device 82. Tubing 81 and tubing 83 represent fluid flow paths previously taken by cellular components, and it may be desirable to return whole blood via both pathways to capture as many residual cells possible for return to the blood source. FIG. 8D depicts one embodiment of a fluid flow path for then rinsing out blood components with plasma or saline from the right cassette 23R. Whole blood from chamber 12 may be pumped into tubing 84 into right cassette 23R via a first pathway 84a within cassette 23R and be pumped out of cassette 23R via a second pathway 85a into tubing 85 back into the separation chamber 12 in a cyclical fashion. Following rinsing of right cassette 23R, whole blood return shown in FIGS. 8B and 8C may be repeated to return whole blood to the blood source.

Without limiting the foregoing description, in accordance with one aspect of the subject matter herein, there is provided a method for prophylaxis or treatment of a graft's rejection of a recipient, at least partially driven and adjusted by a microprocessor-based controller. Provided is a disposable fluid circuit comprising a first product container configured to receive a transplant component and a second product container configured to receive an apoptotic component. Provided is a separator configured to associate with the disposable fluid circuit, the separator comprising a chamber configured to rotate about a rotational axis and convey whole blood into an inlet region of the chamber for separation into a red blood cell component, a plasma component, and a white blood cell component. Whole blood from a blood source is directed into the disposable fluid circuit and the separator. The whole blood is separated into the red blood cell component, the plasma component, and the white blood cell component. A first portion comprising the transplant component of the white blood cell component is directed to the first product container. A second portion of the white blood cell component is directed to the second product container and the second portion is rendered apoptotic.

In accordance with a second aspect which may be used or combined with the immediately preceding aspect, a recipient is connected to the first product container and the second product container. The transplant component from the first product container is infused to the recipient. The apoptotic second portion of the white blood cell component is infused from the second product container to the recipient.

In accordance with a third aspect which may be used or combined with any of the preceding aspects, rendering the second portion apoptotic comprises at least one of 1) mixing a photoactivation agent to the second portion of the white blood cell component and irradiating a mixture comprising the photoactivation agent and the second portion of the white blood cell component; and 2) applying heat and/or cool shocks to the second portion.

In accordance with a fourth aspect which may be used or combined with any of the preceding aspects, the second portion is rendered apoptotic while separating and collecting the first portion comprising the transplant component of the white blood cell component.

In accordance with a fifth aspect which may be used or combined with the second aspect, the apoptotic second portion of the white blood cell component is infused from the second product container to the recipient as late as 3 days prior to infusing the transplant component from the first product container to the recipient.

In accordance with a sixth aspect which may be used or combined with any of the second and fifth aspects, the apoptotic second portion of the white blood cell component is infused from the second product container to the recipient as early as 10 days after infusing the transplant component from the first product container to the recipient.

In accordance with a seventh aspect which may be used or combined with any of the second, fifth, and sixth aspects, the apoptotic second portion of the white blood cell component is infused from the second product container to the recipient after manifestation by the recipient of GvHD symptoms.

In accordance with an eighth aspect, which may be used or combined with any of the second and fifth through seventh aspects, the transplant component and/or the apoptotic second portion is cryopreserved prior to infusing to the recipient.

In accordance with a ninth aspect which may be used or combined with any of the preceding aspects, 1) a first portion of the red blood cell component is returned to the blood source via a first pathway within the fluid circuit; 2) a second portion of the red blood cell component, a first portion of the plasma component, and/or unseparated white blood cell component is returned to the blood source from the chamber via a second pathway within the fluid circuit; 3) a third portion of the red blood cell component, a second portion of the plasma component, and/or unseparated white blood cell component is returned to the blood source from the chamber via a third pathway within the fluid circuit; 4) unseparated white blood cell component is rinsed with saline or plasma along a fourth pathway within the fluid circuit into the chamber; and 5) steps 2 and 3 are repeated.

In accordance with a tenth aspect, which may be used or combined with any of the preceding aspects, the transplant component of the white blood cell component comprises stem cells, and the apoptotic second portion of the white blood cell component comprises apoptotic mononuclear cells.

In accordance with an eleventh aspect, there is provided a system for prophylaxis or treatment of a graft's rejection of a recipient. A donor disposable fluid circuit is in communication with a first product container configured to receive a transplant component. The donor disposable fluid circuit is also in communication with a second product container configured to receive an apoptotic component. A separator is configured to associate with the donor disposable fluid circuit. The separator comprises a chamber configured to rotate about a rotational axis and convey whole blood into an inlet region of the chamber for separation into a red blood cell component, a plasma component, and a white blood cell component. A microprocessor-based controller is in communication with the separator. The controller is configured to direct whole blood from a blood source into the donor disposable fluid circuit and the separator. The whole blood is separated into the red blood cell component, the plasma component, and the white blood cell component. A first portion comprising the transplant component of the white blood cell component is directed to the first product container. A second portion of the white blood cell component is directed to the second product container. The second product container comprising the second portion of the white blood cell component and a photoactivation agent is irradiated to create an apoptotic white blood cell component. A recipient disposable circuit is configured to receive the transplant component from the first product container and the apoptotic white blood cell component from the second container to be infused to a recipient.

In accordance with a twelfth aspect which may be used or combined with the eleventh aspect, the controller is configured to irradiate the second product container while separating and collecting the first portion comprising the transplant component of the white blood cell component.

In accordance with a thirteenth aspect which may be used or combined with any of the eleventh and twelfth aspects, the controller is further configured to infuse the apoptotic white blood cell component from the second product container to the recipient as late as 3 days prior to infusing the transplant component from the first product container to the recipient.

In accordance with a fourteenth aspect which may be used or combined with any of the eleventh through thirteenth aspects, the controller is further configured to infuse the apoptotic white blood cell component from the second product container to the recipient as early as 10 days after infusing the transplant component from the first product container to the recipient.

In accordance with a fifteenth aspect which may be used or combined with any of the eleventh through fourteenth aspects, the controller is further configured to: 1) direct a first portion of the red blood cell component to the blood source via a first pathway within the fluid circuit; 2) direct a second portion of the red blood cell component, a first portion of the plasma component, and/or unseparated white blood cell component to the blood source from the chamber via a second pathway within the fluid circuit; 3) direct a third portion of the red blood cell component, a second portion of the plasma component, and/or unseparated white blood cell component to the blood source from the chamber via a third pathway within the fluid circuit; 4) direct saline or plasma along a fourth pathway within the fluid circuit to capture unseparated white blood cell component within the fourth pathway into the chamber; and 5) repeat steps 2 and 3.

In accordance with a sixteenth aspect which may be used or combined with any of the eleventh through fifteenth aspects, the transplant component comprises stem cells, and the apoptotic white blood cell component comprises apoptotic mononuclear cells.

In accordance with a seventeenth aspect, there is provided a system for prophylaxis or treatment of a graft's rejection of a recipient or a recipient's rejection of a graft. A donor disposable fluid circuit is in communication with a transplant product container configured to receive a transplant component. A recipient disposable fluid circuit is in communication with a recipient product container configured to receive an apoptotic component. A separator is configured to associate with the donor disposable fluid circuit and the recipient disposable circuit. The separator comprises a chamber configured to rotate about a rotational axis and convey whole blood into an inlet region of the chamber for separation into a red blood cell component, a plasma component, and a white blood cell component. A microprocessor-based controller is in communication with the separator. The controller is configured to direct donor whole blood from a donor into the donor disposable fluid circuit and the separator. A donor white blood cell component comprising the transplant component is separated from remaining blood components. The transplant component is directed to the transplant product container. Recipient whole blood is directed from a recipient into the recipient disposable fluid circuit and the separator. The recipient whole blood is separated into a recipient red blood cell component, a recipient plasma component, and a recipient white blood cell component. The recipient white blood cell component is directed to the recipient product container. The recipient product container comprising the recipient white blood cell component and a photoactivation agent is irradiated to create an apoptotic white blood cell component. The apoptotic white blood cell component from the recipient product container is infused into the recipient disposable circuit to the recipient.

In accordance with an eighteenth aspect which may be used or combined with the seventeenth aspect, the controller is further configured to infuse the apoptotic white blood cell component from the recipient product container to the recipient as late as 3 days prior to and as early as 10 days after infusing the transplant component from the transplant product container to the recipient.

In accordance with a nineteenth aspect, which may be used or combined with any of the seventeenth through eighteenth aspects, the transplant component comprises stem cells, and the apoptotic white blood cell component comprises apoptotic mononuclear cells.

While described with reference to extracorporeal photopheresis, stem cell transplantation, and an apheresis device, the subject matter presented herein may be applied to other apoptosis-rendering processes (e.g., temperature shocks, UVC light, gamma irradiation, pressure, etc.), transplantation of other organs/grafts (kidney, lung, skin, etc.), or other medical devices (e.g., internal or external infusion pumps, dialysis machines, offline irradiation, etc.). In some embodiments, the teachings herein could be used on any medical device that involves a recipient receiving blood components or biological components originating from someone other than the recipient.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A method for prophylaxis or treatment of a graft's rejection of a recipient, at least partially driven and adjusted by a microprocessor-based controller, comprising the steps of:
   mounting a disposable fluid circuit comprising a first product container and a second product container onto a separator configured to associate with said disposable fluid circuit, the separator comprising a chamber configured to rotate about a rotational axis and convey whole blood into an inlet region of the chamber for separation into a red blood cell component, a plasma component, and a white blood cell component;
   directing whole blood from a blood source into the disposable fluid circuit and the chamber;
   separating the whole blood into the red blood cell component, the plasma component, and the white blood cell component;
   directing a first portion comprising a transplant component of the white blood cell component to the first product container;
   directing a second portion of the white blood cell component to the second product container and rendering the second portion apoptotic;
   connecting a recipient to the first product container and the second product container;
   infusing the transplant component from the first product container to the recipient; and
   infusing the apoptotic second portion of the white blood cell component from the second product container to the recipient as late as 3 days prior to infusing the transplant component from the first product container to the recipient or as early as 10 days after infusing the transplant component from the first product container to the recipient.

2. The method of claim 1, wherein rendering the second portion apoptotic comprises at least one of:
   1) mixing a photoactivation agent to the second portion of the white blood cell component and irradiating a mixture comprising the photoactivation agent and the second portion of the white blood cell component; and
   2) applying heat and/or cool shocks to the second portion.

3. The method of claim 1, further comprising rendering the second portion apoptotic while separating and collecting the first portion comprising the transplant component of the white blood cell component.

4. The method of claim 1, further comprising infusing the apoptotic second portion of the white blood cell component from the second product container to the recipient after manifestation by the recipient of GvHD symptoms.

5. The method of claim 1, further comprising cryopreserving the transplant component and/or the apoptotic second portion prior to infusing to the recipient.

6. The method of claim 1, further comprising:
   1) returning a first portion of the red blood cell component to the blood source via a first pathway within the fluid circuit;
   2) returning a second portion of the red blood cell component, a first portion of the plasma component, and/or an unseparated white blood cell component to the blood source from the chamber via a second pathway within the fluid circuit;
   3) returning a third portion of the red blood cell component, a second portion of the plasma component, and/or the unseparated white blood cell component to the blood source from the chamber via a third pathway within the fluid circuit;
   4) rinsing the unseparated white blood cell component with saline or plasma along a fourth pathway within the fluid circuit into the chamber; and
   5) repeating steps 2 and 3.

7. The method of claim 1, wherein the transplant component of the white blood cell component comprises stem cells, and the apoptotic second portion of the white blood cell component comprises apoptotic mononuclear cells.

* * * * *